United States Patent [19]

Müllner et al.

[11] Patent Number: 5,461,035

[45] Date of Patent: Oct. 24, 1995

[54] SHORT PEPTIDES WITH INSULIN ACTIVITY

[75] Inventors: Stefan Müllner, Hochheim am Main; Wolfgang König, Hofheim am Taunus; Günter Müller, Frankfurt am Main, all of Germany

[73] Assignee: Hoechst Aktiengesellschaft, Frankfurt am Main, Germany

[21] Appl. No.: 285,443

[22] Filed: Aug. 4, 1994

Related U.S. Application Data

[63] Continuation of Ser. No. 805,899, Dec. 12, 1991, abandoned.

[30] Foreign Application Priority Data

Dec. 19, 1990 [DE] Germany ................ 40 40 574.5

[51] Int. Cl.$^6$ .................. A61K 38/00; C07K 5/00; C07K 7/00; C07K 17/00
[52] U.S. Cl. ................ 514/16; 514/17; 514/18; 530/328; 530/329; 530/330; 530/331
[58] Field of Search .................. 514/16, 17, 18; 530/328, 329, 330, 331

[56] References Cited

U.S. PATENT DOCUMENTS

| | | |
|---|---|---|
| 4,212,796 | 7/1980 | Konig . |
| 4,215,037 | 7/1980 | Konig . |
| 4,499,080 | 2/1985 | Duflot et al. .............. 514/12 |

FOREIGN PATENT DOCUMENTS

| | | |
|---|---|---|
| 0147942 | 4/1981 | German Dem. Rep. . |
| 2740406A1 | 3/1979 | Germany . |
| 2801175A1 | 7/1979 | Germany . |

OTHER PUBLICATIONS

Spector et al., i Biochem Biophys Res. Comm., vol. 150, No. 1, Jan. 1988, pp. 156–162.
Korshunora et al., i Chem Abstrs., vol. 79, p. 390: 42822f, 1973.
Insulin Resistance And Noninsulin–Dependent Diabetes Millitus: Which Horse Is Pulling The Cart?, Garvey, Diabetes/Metabolism Reviews, vol. 5 No. 8, pp. 727–742 (1989).
H. A. Saroff et al., "The Uniqueness of Protein Sequences. o–Uniqueness and Infrequent Peptides, " Bulletin of Mathematical Biology, vol. 45, No. 1, pp. 117–138, 1983.
M. Christensen et al., "Substituted Benzhydrylamine Resins in Solid Phase Peptide Synthesis of Peptide Amides and Peptides with C–Terminal Asparagine Monitored by Potentiometric Titration with Perchloric Acid. Classification of Acid Lability of Different Resins, " Acta Chemica Scandinavica B 35, pp. 573–581, 1981.
Chemical Abstracts No. 193628, vol. 91, p. 680, 1979.
Chemical Abstracts No. 21087, vol. 91, p. 714, 1979.
W. Konig et al., "Saure Abspaltung der S–Tritylgruppe am Beispiel synthetischer Insulinfragmente, " Liebigs Ann. Chem., pp. 227–247, 1979.
Chemical Abstracts, vol. 91(23) abstract 91:193628w (1979).
Chemical Abstracts, vol. 93(11) abstract 93:114962r (1980).
EPO Search Report, EP 91121624.0.

*Primary Examiner*—Jill Warden
*Assistant Examiner*—A. M. Davenport
*Attorney, Agent, or Firm*—Finnegan, Henderson, Farabow, Garrett & Dunner

[57] ABSTRACT

A method for the treatment of diabetes mellitus or non-insulin-dependent diabetes comprising at least one peptide selected from the group consisting of Tyr-Gln-Leu-Glu-Asn-Tar-Cys-Asn, Acetyl-Leu-Glu-Asn-Tar-Cys-Asn OH, Asn-Tar-Cys-Asn, or a peptide of the formula $$X\text{-}Q\text{-}Cys\text{-}D \qquad (II)$$

or the stereoisomeric forms of the peptide of formula II, or the physiologically tolerated salts of the peptide of the formula II.

3 Claims, No Drawings

SHORT PEPTIDES WITH INSULIN ACTIVITY

This application is a continuation of application Ser. No. 07/805,899, filed Dec. 12, 1991, now abandoned.

The invention relates to novel peptides which have insulin activity and are suitable for the treatment of diabetes mellitus.

Insulins are composed of two polypeptide chains, the A chain which contains 21 amino-acid residues, and the B chain with 30 amino-acid residues. The A and B chain are connected together by two disulfide bridges, with the cysteine residues in position A7 and B7, and A20 and B19, being linked together. There is a third disulfide bridge between A6 and A11. Animal and human insulins are produced in the pancreas in the form of preproinsulins. Human preproinsulin is composed, for example, of a prepeptide with 24 amino-acid residues to which is attached a proinsulin with 86 amino-acid residues with the following configuration: prepeptide-B-Arg-Arg-C-Lys-Arg-A where C is an amino-acid chain of 31 residues. During excretion from the islets of Langerhans, the prepeptide is cleaved off to give proinsulin. Finally the C chain undergoes proteolytic cleavage to give active human insulin.

Insulin has a large number of effects on insulin-sensitive tissue. One noteworthy effect is the rapid reduction of the glucose level in meals when insulin is used. This is brought about by rapid uptake of glucose from the blood by myocytes and lipocytes. Insulin furthermore activates glycogen synthetase and inhibits lipolysis. Insulin promotes protein synthesis from amino acids and enhances the induction of glycokinase and phosphofructokinase and inhibits the formation of certain enzymes of gluconeogenesis such as pyruvate carboxylase and fructose diphosphatase.

Type II diabetes, non-insulin-dependent diabetes, is associated with insulin resistance of peripheral tissue such as muscle or adipose tissue. The resulting reduction in glucose utilization is caused by lack of insulin stimulation of glucose transport and subsequent metabolic processes. This multiple resistance suggests a defect at the receptor or post-receptor level, i.e. before production of the second messenger (Garvey, Diabetes/Metabolism Reviews, 5, (1989), 727–742).

It has now been found, surprisingly, that short peptides may have insulin activity and are suitable for the treatment of diabetes mellitus.

The invention thus relates to peptides of the formula I

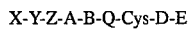      (I)

where
A is
 a) an amino acid or a covalent bond,
B is
 a) an amino acid or a covalent bond,
Q is
 a) an amino acid
 b) an aromatic amino acid substituted one or more times on the ring by
  1) $R^1$ where $R^1$ is
   1.1 $(C_1-C_{18})$-alkyl,
   1.2 $(C_3-C_{18})$-cycloalkyl,
   1.3 $(C_6-C_{14})$-aryl,
   1.4 $(C_6-C_{41})$-aryl substituted one or more times by
    1.4.1 $(C_1-C_1)$-alkyl or
   1.5 $(C_1-C_8)$-alkyl substituted one or more times by
    1.5.1 $(C_6-C_{14})$-aryl,
  2) $R^2$ where $R^2$ is
   2.1 $(C_1-C_{18})$-alkyl,
   2.2 $(C_3-C_{18})$-cycloalkyl,
   2.3 $(C_1-C_{18})$-alkoxy,
   2.4 $(C_3-C_{14})$-cycloalkoxy,
   2.5 $(C_6-C_{14})$-aryl,
   2.6 $(C_6-C_{14})$-aryl substituted one or more times by
    2.6.1 $(C_1-C_8)$-alkyl,
    2.6.2 $(C_1-C_8)$-alkoxy,
   2.7 $(C_6-C_{14})$-aryloxy,
   2.8 $(C_6-C_{14})$-aryloxy substituted one or more times by
    2.8.1 $(C_1-C_8)$-alkyl,
    2.8.2 $(C_1-C_8)$-alkoxy,
   2.9 $(C_1-C_8)$-alkyl substituted one or more times by
    2.9.1 $(C_6-C_{14})$-aryl,
   2.10 $(C_1-C_8)$-alkoxy substituted one or more times by
    2.10.1 $(C_6-C_{14})$-aryl,
   2.11 halogen such as fluorine, chlorine, bromine or iodine,
   2.12 nitro or
   2.13 trifluoromethyl,
  c) a covalent bond
D is
 a) an amino acid,
 b) a C-terminal amino group $—NR^3_2$ where $R^3$ can be identical or different and is
  1) $(C_1-C_3)$-alkyl,
  2) $(C_1-C_3)$-alkyl substituted one or more times by
   2.1 fluorine,
   2.2 hydroxyl group,
  3) cyclopropyl,
  4) cyclopropyl substituted one or more times by
   4.1 fluorine,
   4.2 hydroxyl group or
  5) hydrogen atom,
 c) a covalent bond,
E is
 a) an amino acid,
 b) a covalent bond or
 c) C-terminal amino group $—NR^3_2$ where $R^3$ can be identical or different and have the above-mentioned meaning,
X is
 a) hydrogen,
 b) $R^1$-CO where $R^1$ has the abovementioned meaning,
 c) $(C_1-C_{18})$-alkoxy-CO,
 d) $(C_3-C_{18})$-cycloalkoxy-CO or
 e) $(C_6-C_{14})$-aryl-$(C_1-C_8)$-alkoxy-CO,
Y is an amino acid or a covalent bond
Z is an amino acid or a covalent bond
or dimers of the peptides of the formula I with cystine as dimerization component, the stereoisomeric forms thereof where appropriate, or physiologically tolerated salts of the peptide of the formula I, excepting the compound H-Tyr-Gln-Leu-Glu-Asn-Tyr-Cys-Asn-OH (SEQ ID No. 1) or H-Leu-Glu-Asn-Tyr-Cys-Asn-OH. (SEQ ID No. 2)

Preferred peptides of the formula I are those in which
A is Glu, pGlu, Gln, Leu, Met, Arg, Lys or Orn,
B is Asn, Thr, Ser, Gly, Ala, Val or Ile,
C is Tyr, Tyr($R^1$), Phe($R^2$), Trp($R^2$) or Nal,
D is Asp, Asn, D-Asp, D-Asn, bAla, Azagly-$NH_2$ or NH—$R^3$,
E is $NH_2$, Asp, Asn, Glu or Gln, X is hydrogen or an acyl radical,
R$^1$, R$^2$ and R$^3$ have the abovementioned meaning,
Y is tyrosine or a covalent bond, and
Z is glutamine, leucine or a covalent bond.

Particularly preferred peptides have the formula II $$X\text{-}Q\text{-}Cys\text{-}D \qquad (II)$$

where
Q is Tyr, Tyr(R$^1$), Phe(R$^2$), Trp(R$^3$) or Nal
D is Asp, Asn, D-Asp, D-Asn, bAla, Azagly-NH$_2$ or NH—R$^3$, and
X
is a) hydrogen,
b) R$^1$—CO,
c) (C$_1$–C$_{18}$)-alkoxy-CO,
d) (C$_3$–C$_{18}$)-cycloalkoxy-CO or
e) (C$_6$–C$_{14}$)-aryl-(C$_1$–C$_8$)-alkoxy-CO,
or dimers of the peptides of the formula I with cystine as dimerization component and R$^1$, R$^2$ and R$^3$ have the abovementioned meaning, the stereoisomeric forms thereof where appropriate, or physiologically tolerated salts of the peptide of the formula II.

Especially preferred peptides are
Asn Tyr Cys Asn (SEQ ID No. 3) or Tyr Cys Asn (SEQ ID No. 4)

The term amino acids means, for example, the stereoisomeric forms, i.e. D or L forms, of the following compounds:

| | | |
|---|---|---|
| alanine | glycine | proline |
| cysteine | histidine | glutamine |
| aspartic acid | isoleucine | arginine |
| glutamic acid | lysine | serine |
| phenylalanine | leucine | threonine |
| | methionine | valine |
| | asparagine | tryptophan |
| | | tyrosine |
| 2-aminoadipic acid | 2-aminoisobutyric acid | |
| 3-aminoadipic acid | 3-aminoisobutyric acid | |
| beta-alanine | 2-aminopimelic acid | |
| 2-aminobutyric acid | 2,4-diaminobutyric acid | |
| 4-aminobutyric acid | desmosine | |
| piperidinecarboxylic acid | 2,2-diaminopimelic acid | |
| 6-aminocaproic acid | 2,3-diaminopropionic acid | |
| 2-aminoheptanoic acid | N-ethylglycine | |
| 2-(2-thienyl)glycine | 3-(2-thienyl)alanine | |
| penicillamine | | |
| N-ethylasparagine | sarcosine | |
| hydroxylysine | N-methylisoleucine | |
| allo-hydroxylysine | 6-N-methyllysine | |
| 3-hydroxyproline | N-methylvaline | |
| 4-hydroxyproline | norvaline | |
| isodesmosine | norleucine or | |
| allo-isoleucine | ornithine | |
| N-methylglycine | | |

The amino acids are abbreviated in the generally customary manner (cf. Schröder, Lübke, The Peptides, Volume I, New York 1965, pages XXII–XXIII; Houben-Weyl, Methoden der Org. Chemie (Methods of Org. Chemistry) Volume XV/1 and 2 Stuttgart 1974).

The amino acid pGlu is pyroglutamyl, Nal is 3-(2-naphthyl)alanine, Azagly-NH$_2$ is a compound of the formula NH$_2$—NH—CONH$_2$ and D-Asp is the D form of aspartic acid. Peptides are according to their chemical nature amides and decompose to amino acids on hydrolysis.

Cycloalkyl also means alkyl-substituted radicals such as, for example, 4-methylcyclohexyl or 2,3-dimethylcyclopentyl.

Examples of C$_6$–C$_{14}$-aryl are phenyl, naphthyl, biphenylyl or fluorenyl; phenyl and naphthyl are preferred. Corresponding statements apply to radicals derived therefrom, such as, for example, aryloxy, aralkyl and aralkoxy. Aralkyl means, for example, an unsubstituted or substituted C$_6$–C$_{14}$-aryl radical which is linked to C$_1$–C$_8$-alkyl, such as, for example, benzyl, 1- and 2-naphthylmethyl, halobenzyl and alkoxybenzyl, it not being the intention, however, to restrict aralkyl to the said radicals.

The term alkyl means straight-chain or branched hydrocarbon chains. A corresponding statement applies to radicals derived therefrom, such as, for example, alkoxy, aralkyl and alkanoyl.

Physiologically tolerated salts of the compound of the formula I mean, in particular, pharmaceutically utilizable or non-toxic salts. Salts of this type are formed, for example, by compounds of the formula I which contain acid groups, for example carboxyl, with alkali metals or alkaline earth metals such as, for example, Na, K, Mg and Ca, and with physiologically tolerated organic amines such as, for example, triethylamine and tris(2-hydroxyethyl)amine. Compounds of the formula I which contain basic groups, for example an amino group or a guanidino group, form salts with inorganic acids such as, for example, hydrochloric acid, sulfuric acid or phosphoric acid and with organic carboxylic or sulfonic acids such as, for example, acetic acid, citric acid, benzoic acid, maleic acid, fumaric acid, tartaric acid and p-toluenesulfonic acid. Compounds in which basic and acidic groups are present in equal number form internal salts and do not depend on a third salt component.

The invention furthermore relates to a process for the preparation of peptides of the formula I, which comprises
a) reacting a segment with C-terminal free carboxyl group or the activated derivative thereof with a corresponding segment with N-terminal free amino group or
b) synthesizing the peptide stepwise, eliminating in the compound obtained as in (a) or (b) where appropriate one or more protective groups temporarily introduced to protect other functions, and converting the compounds of the formula I obtained in this way where appropriate into their physiologically tolerated salt.

The peptides according to the invention are prepared by the general methods of peptide chemistry stepwise from the C-terminal end or by coupling of segments (Houben-Weyl, Methoden der Organischen Chemie, Volume 15/1,2). The peptide couplings can be carried out, for example, by the mixed anhydride method, via active esters, azides or by the carbodiimide method, in particular with the addition of substances which increase the reaction rate and prevent racemization, such as, for example, 1-hydroxybenzotriazole, N-hydroxysuccinimide, 3-hydroxy-4-oxo-3,4-dihydro-1,2, 3-benzotriazine, N-hydroxy-5-norbornene- 2,3-dicarboximide, also with the use of active derivatives of 1-hydroxybenzotriazole or anhydrides of phosphoric, phosphonic and phosphinic acids at a reaction temperature between −10° C. and the boiling point of the solvent, preferably between −5° C. and 40° C.

Solvents suitable for this purpose are dimethylformamide, dimethylacetamide, N-methylpyrrolidone or dimethyl sulfoxide.

It is also possible to employ solvents such as methylene chloride, chloroform or tetrahydrofuran where the solubility of the components permits it. The said methods are described, for example, in Meienhofer-Gross: "The Peptides" Academic Press, Vol. I (1979).

If necessary to prevent side reactions or for the synthesis of specific peptides, the functional groups in the side chain of amino acids are additionally protected by suitable protective groups (see, for example, T. W. Greene, "Protective Groups in Organic Synthesis"), primarily employing
Arg(Tos), Arg(Mts), Arg(Mtr), Arg(PMC), Asp(OBzl), Asp(OBut), Cys-(4-MeBzl), Cys(Acm), Cys(SBut), Glu-(OBzl), Glu(OBut), His(Tos), His(Fmoc), His(Dnp), His-(Trt), Lys(Cl-Z), Lys(Boc), Met(O), Ser(Bzl), Ser(But), Thr(Bzl), Thr(But), Trp(Mts), Trp(CHO), Tyr(Br-Z), Tyr-(Bzl) or Tyr(But).

Preferably used as amino-protective groups are the benzyloxycarbonyl (Z) radical which can be eliminated by catalytic hydrogenation, the 2-(3,5-dimethyloxyphenyl)-2-propyloxycarbonyl (Ddz) or trityl (Trt) radical which can be eliminated by weak acids, and the 9-fluorenylmethyloxycarbonyl (Fmoc) radical which can be eliminated by secondary amines. The SH group of cysteine can be blocked by a number of protective groups. Preferred for this are the trityl (Trt) radical and the S-tert-butyl (StBu) radical. The trityl radical can be eliminated by iodine oxidation with the formation of the cysteine compounds or by reducing acidic cleavage to give the cysteine compounds (Liebigs Ann. Chem. 1979, 227–247).

On the other hand, the S-tert-butyl radical is best subjected to reductive cleavage with tributylphosphine (Aust. J. Chem. 19 (1966) 2355–2360). OH and COOH functions in the side chains are best protected by the tert-butyl (tBu) radical which can be eliminated with acid (see also: Meienhofer-Gross: "The Peptides", Vol 3)

The compounds of the formula I or II and the physiologically tolerated salts thereof are primarily used as active substances for pharmaceutical compositions for the treatment of diabetes mellitus or non-insulin-dependent diabetes.

The invention therefore also relates to a pharmaceutical composition which contains at least one compound of the formula I or II and/or at least one of its physiologically tolerated salts in dissolved, amorphous and/or crystalline— preferably in amorphous and/or crystalline—form, the compounds H-Leu-Glu-Asn-Tyr-Cys-Asn-OH (SEQ ID No. 2) and H-Tyr-Gln-Leu-Glu-Asn-Tyr-Cys-Asn-OH (SEQ ID No. 1) not being excepted.

The peptides preferred for this pharmaceutical composition are
Asn Tyr Cys Asn (SEQ ID No. 3), H-Tyr-Gln-Leu-Glu-Asn-Tyr-Cys-Asn-OH (SEQ ID No. 1) or Tyr Cys Asn (SEQ ID No. 4) and/or the physiologically tolerated salts thereof.

The pharmaceutical composition is preferably a solution or suspension for injection with a pH between about 3.0 and 9.0, preferably between about 5.0 and 8.5, which contains a suitable isotonicizing agent, a suitable preservative and, where appropriate, a suitable buffer, and, where appropriate, also a depot principle, all of course in sterile aqueous solution or suspension. The totality of the constituents of the composition apart from the active substance forms the composition vehicle.

Examples of suitable isotonicizing agents are glycerol, glucose, mannitol, NaCl, calcium or magnesium compounds such as, for example, $CaCl_2$ or $MgCl_2$.

Examples of suitable preservatives are phenol, m-cresol, benzyl alcohol and/or p-hydroxybenzoic esters.

Examples of buffer substances which can be used, in particular for adjusting to a pH between about 5.0 and 8.5, are sodium acetate, sodium citrate, sodium phosphate etc. Otherwise suitable for adjusting the pH are also physiologically acceptable dilute acids (typically HCl) or alkalis (typically NaOH).

It is also possible for modified (cf. EP-B 132 769 and EP-B 132 770) and/or unmodified insulins, preferably beef, pork or human insulin, especially human insulin, to be admixed for the purpose of altering the profile of action of the composition according to the invention.

The pharmaceutical composition is prepared by converting at least one compound of the formula I or II and/or at least one of the physiologically tolerated salts thereof, where appropriate together with modified and/or unmodified insulins or derivatives thereof, with a physiologically acceptable vehicle and, where appropriate, with suitable additives and auxiliaries, into a suitable dosage form.

The invention is now explained in detail by the following examples.

Example 1

H-Tyr-Cys-Asn-OH (SEQ ID No. 4)
1a. Fmoc-Tyr(tBu)-Cys(Trt)-Asn-OtBu 1.63 g of DCC are added to a stirred solution of 3.4 g of Fmoc-Tyr(tBu)-OH, 3.95 g (7.4 mmol) of H-Cys(Trt)-Asn-OtBu (Liebigs Ann. Chem. 1979, 242) and 1 g of HOBT in 50 ml of dimethylformamide at 0° C., and the mixture is left to stir at 0° C. for 1 h and to stand at room temperature overnight. The next day, the precipitate is filtered off with suction and the filtrate is concentrated. The residue is triturated with ethyl acetate. Yield 2.83 g. A further 3.63 g can be isolated from the mother liquor. Total yield: 6.46 g (89%).

$C_{58}H_{62}N_4O_8S$ (975.218)
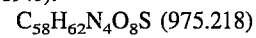
Melting point 112°–114° C., $[\alpha]_D^{21} = -15.3°$ (c=1, in methanol).

1b. H-Tyr (tBu)-Cys (Trt)-Asn-OtBu 6 g (6.15 mol) of Fmoc-Tyr(tBu)-Cys(Trt)-Asn-OtBu are dissolved in 100 ml of dimethylformamide. To this are added 6.8 g of diethylamine, and the mixture is left to stand at room temperature for 10 minutes. It is subsequently concentrated under high vacuum, and the residue is chromatographed on silica gel with methylene chloride. Lipophilic impurities are eluted with methylene chloride. The substance is eluted with methylene chloride/methanol 9.5:0.5. Yield 4.4 g of oil (95%).

$C_{43}H_{52}N_4O_6S$ (752.976)

1c. H-Tyr-Cys-Asn-OH (SEQ ID No. 4)

2.2 g (2.9 mmol) of H-Tyr(tBu)-Cys(Trt)-Asn-OtBu are dissolved in a mixture of 25 ml of trifluoroacetic acid and 25 ml of ethyl mercaptan. After 4 hours, the mixture is tipped into 250 ml of water. The aqueous solution is extracted 3 times with ether and freeze-dried. Yield 1.05 g (91%).

$C_{16}H_{22}N_4O_6S$ (398.44)
$[\alpha]_D^{23} = -1.1°$ (C=1 in water)

Example 2

H-Asn-Tyr-Cys-Asn-OH (SEQ ID No. 3)
2a. Fmoc-Asn-Tyr(tBu)-Cys(Trt)-Asn-OtBu.

0.64 g of DCC is added to a stirred solution of 2.2 g (2.9 mmol) of H-Tyr(tBu)-Cys(Trt)-Asn-OtBu, 1.04 g of Fmoc-Asn-OH, 0.39 g of HOBt in 30 ml of dimethylformamide at 0° C. The mixture is left to stir at 0° C. for 1 h and to stand at room temperature overnight. The next day the precipitate is filtered off with suction and the filtrate is concentrated. The residue is dissolved in ethyl acetate and extracted successively with water, saturated $NaHCO_3$ solution, $KHSO_4$ solution and water, dried over $Na_2SO_4$ and concentrated. The residue is triturated with petroleum ether. Yield 1.98 g (63%). $C_{62}H_{68}N_6O_{10}S$ (1089.323), $[\alpha]_D^{22} = -18.8°$ (c=1, in methanol)

2b. H-Asn-Tyr(tBu)-Cys(Trt)-Asn-OtBu 1.9 g (1.74 mmol) of Fmoc-Asn-Tyr(tBu)-Cys(Trt)-Asn-OtBu are dissolved in 50 ml of dimethylformamide. To this are added 1.8 ml of diethylamine, and the mixture is left to stand at room temperature for 15 minutes. It is then concentrated under high vacuum, and the residue is triturated with ethyl acetate and dried in vacuo. Yield 0.98 g (65%). $C_{47}H_{58}N_6O_8S$ (867.081), $[\alpha]_D^{21}=-7.2°$ (c=1, in methanol)

2c. H-Asn-Tyr-Cys-Asn-OH (SEQ ID No. 3)

0.9 g (1 mmol) of the compound obtained above is dissolved in a mixture of 10 ml of ethyl mercaptan and 10 ml of trifluoroacetic acid. After 4 hours, the mixture is poured into 100 ml of water. The aqueous solution is extracted 3 times with ether and freeze-dried. Yield 455 mg (89%).

$C_{20}H_{28}N_6O_8S$ (512.547)
$[\alpha]_D^{23}=-26.0°$ (c=1, in water)

Example 3

Acetyl-Leu-Glu-Asn-Tyr-Cys-Asn-OH 0.4 ml of N-ethylmorpholine and 0.53 g of acetyl-N-hydroxysuccinimide are added to a solution of 2.0 g (1.56 mmol) of H-Leu-Glu(OtBu)-Asn-Tyr(tBu)-Cys(Trt)-Asn-OtBu.trifluoroacetate (Liebigs Ann. Chem. 1979, 243) in 30 ml of dimethylformamide. After a reaction time of 4 h at room temperature, the mixture is concentrated under high vacuum. The residue is dissolved in ethyl acetate and extracted by shaking successively with saturated $NaHCO_3$ solution, $KHSO_4$ solution and water. This results in a precipitate, which is filtered off with suction. Yield 1.3 g. The ethyl acetate phase is dried over $Na_2SO_4$ and concentrated. The residue is triturated with diethyl ether and filtered with suction. Yield 0.8 g. Total yield 2.1 g (>100%).

The 1.3 g (about 1.07 mmol) of the pure batch of Ac-Leu-Glu(OtBu)-Asn-Tyr(tBu)-Cys(Trt)-Asn-OtBu obtained above are dissolved in a mixture of 30 ml of trifluoroacetic acid and 30 ml of ethyl mercaptan. After a reaction time of 4 h, the mixture is tipped into 300 ml of water, and the aqueous solution is extracted 3 times with diethyl ether. The aqueous phase is freeze-dried. Yield 740 mg (87%).

$C_{33}H_{48}N_8O_{13}S$ (796.86)
$[\alpha]_D^{23}=-25.1°$ (c=1, in water)

Example 4

Synthesis of H-Tyr(Bu')-Gln-Leu-Glu(OBu')-Asn-Tyr(Bu')-Cys(Trt-Asn-Obu'.HBr (7.HBr)

4a. Ddz-Tyr(Bu')-Gln-ONb (16)

6.4 ml (50 mmol) of N-ethylmorpholine and 10.5 g of dicyclohexylcarbodiimide are added to a solution of 25.24 g (55 mmol) of Ddz-Tyr(Bu')-OH, 15.88 g (50 mmol) of H-Gln-ONb. HCl and 6.75 g of 1-hydroxybenzotriazole hydrate in 100 ml of N,N-dimethylformamide at −3° C. The mixture is left to stir at 0° C. for 1 h and at room temperature for 6 h and to stand at room temperature overnight. The precipitate is filtered off with suction, and the filtrate is concentrated. The resulting oil is dissolved in ethyl acetate, and the solution is washed successively with $NaHCO_3$ solution, citrate buffer (pH 3) and water, dried over $Na_2SO_4$ and concentrated. The oily product is triturated with petroleum ether to give a powder which is filtered off with suction. It is then boiled, and decanted, 3 times with 100 ml of diisopropyl ether each time. It is finally triturated with cold diisopropyl ether, filtered off with suction and washed with petroleum ether. Yield 32.8 g (91%); melting point 80°–90° C., $[\alpha]_D^{22}=+15.1°$ (c=1, in methanol).

$C_{37}H_{46}N_4O_{11}$ (722.81)
Calc. C 61.48 H 6.41 N 7.75
Found C 61.3 H 6.7 N 7.9

4b. Ddz-Tyr(Bu')-Gln-OH.dicyclohexylamine 5 ml of water and $Pd/BaSO_4$ are added to a solution of 32.5 g (45 mmol) of 16 in 500 ml of methanol, and hydrogenation is carried out for 7 h. The catalyst is then filtered off with suction, and the filtrate is concentrated. The remaining oil is dissolved in 250 ml of ethyl acetate. To this are added 11.3 ml (55 mmol) of dicyclohexylamine, the mixture is left to stand at 3° C. for some hours, and the precipitate is filtered off with suction. It is triturated with ethyl acetate in a mortar, filtered off with suction and dried in vacuo. Yield 27 g (78%); melting point 170°–171° C., $[\alpha]_D^{23}=+10.2°$ (C=1, in methanol).

$C_{42}H_{64}N_4O_9$ (769.0)
calc. C 65.6 H 8.39 N 7.28
found C 65.4 H 8.5 N 7.3

4c. Ddz-Tyr(Bu')-Gln-OH (17)

2.9 g (3.7 mmol) of Ddz-Tyr(Bu')-Gln-OH.dicyclohexylamine are partitioned between ethyl acetate and citrate buffer (pH 3). The ethyl acetate phase is washed with water until neutral, dried over $Na_2SO_4$ and concentrated. The residue is amorphous 17.

Yield 2 g (90%); melting point 110°–115° C., $[\alpha]_D^{22}=+19.8$ (c=1, in methanol).

$C_{30}H_{41}N_3O_9$ (587.68)
calc. C 61.31 H 7.03 N 7.15
found C 60.6 H 7.2 N 7.0

4d. Ddz-Tyr(Bu')-Gln-Leu-Glu(OBu')-Asn-Tyr(Bu')-Cys(Trt)-Asn-OBu' (18)

9.7 g (16.5 mmol) of 17, 19.2 g (15 mmol) of the compound from Example 3 and 2.025 g (15 mmol) of HOBt are dissolved in 30 ml of N,N-dimethylformamide by stirring at room temperature. The mixture is cooled 0° C., 1.95 ml (15 mmol) of N-ethylmorpholine and a solution of 3.3 g (16 mmol) of dicyclohexylcarbodiimide in 9 ml of N,N-dimethylformamide are added, the mixture is left to stir at 0° C. for 1 h and at room temperature for 4 h and to stand at room temperature overnight, and the dicyclohexylurea is filtered off with suction. It is then washed twice with 4.5 ml of N,N-dimethylformamide each time. The filtrate is allowed to run into 159 ml of saturated $NaHCO_3$ solution with stirring, and the stirring is continued until a powdery precipitate has been produced. This is filtered off with suction, triturated with citrate buffer (pH 3), filtered off with suction, washed with water until neutral and dried under about 0.1 torr (yield 23.1 g). The crude substance is heated almost to boiling on a steam bath, the thin suspension is stored at 3° C. overnight, and the precipitate is filtered off with suction and washed with ethyl acetate and ether.

Yield 20 g (76.8%), $[\alpha]_D^{22}=-10.2°$ (c=1, in methanol).

The substance decomposes above 205° C. and chars at about 250° C. Amino-acid analysis: Asp 2.00; Glu 2.01; Cys 0.75; Leu 0.99; Tyr 1.95

$C_{92}H_{123}N_{11}O_{20}S$ (1735.15)
calc. C 63.68 H 7.15 N 8.88 S 1.85
found C 62.0 H 7.2 N 8.6 S 2.1

4e. H-Tyr(Bu')-Gln-Leu-Glu(OBu')-Asn-Tyr(Bu')-Cys(Trt)-Asn-OBu').HBr (7.HBr)

3.5 g (2 mmol) of 18 are dissolved in a stirred mixture of 1.75 ml of trifluoroacetic acid (20 mmol), 0.35 ml of water and 33 ml of methylene dichloride (about 35 ml of a 5% trifluoroacetic acid solution with 1% water) and 3.5 ml of anisole. The mixture is left to stir at room temperature for 3 h, 2 ml (24.8 mmol) of pyridine are added, and the mixture is concentrated under about 0.1 torr. The residue is triturated with ether, filtered off with suction, washed with ether, dried, triturated with water, filtered off with suction, washed with water and dried over $P_2O_5$ (yield 3.35 g). For further purification, the substance is briefly boiled, and filtered hot with suction, twice with 20 ml of ethyl acetate each time. It is then washed with ether.

Yield 3.0 g (92%); melting point 255°–265° C. (decomp.), $[\alpha]_D^{22}=-20.2°$ (c=1, in methanol).

Amino-acid analysis: Asp 1.97; Glu 2.00; Cys 0.61; Leu 1.00; Tyr 2.01.

$C_{80}H_{110}BrN_{11}O_{16}S$ (1593.8)
calc. C 60.23 H 6.96 N 9.67 S 2.01
found C 60.6 H 7.0 N 9.5 S 2.2

Example 5

The biological activity of the peptides according to the invention, of the formula I and II, is determined using lipocytes and pieces of diaphragm obtained by dissection from rats. The term tripeptide means Tyr Cys Asn-OH and hexapeptide means acetyl-Leu Glu Asn Tyr Cys Asn-OH. The term "baseline" means the activity without stimulation, insulin means human insulin and dpm means radioactive disintegrations per minute. The term peptid denotes peptides having insulin activity according to the present invention. Rat lipocytes were prepared as follows:

Epididymal adipose tissue (Wistar rat, 160–180 g, no feed restriction) is digested with collagenase, and the resulting single lipocytes are washed several times by flotation.

Preparation of pieces of diaphragm from rats: small pieces of tissue (5 mm diameter) are punched out of hemidiaphragms (Wistar rat, 60–70 g, no feed restriction) washed several times.

The two following tests measure the glucose uptake which can be stimulated by insulin and which requires the functional insulin signal-transmission cascade and glucose transport, irrespective of whether glucose is metabolized by oxidation (glycolysis, pentose phosphate pathway) or not by oxidation. The conversion into lipids, glycogen or membrane-impermeable intermediates (glucose 6-phosphate), but not the production of lactate, is followed.

a) Rat lipocytes are incubated in the presence or absence of insulin or peptide with D-[U-$^{14}$C]-glucose (final concentration of D-glucose 22 μM). The cells are separated from the medium by centrifugation through a silicone oil layer and are reisolated, and the cell-associated radioactivity is determined.

b) Pieces of diaphragm are incubated in the presence or absence of insulin or peptide with D-[U-$^{14}$C]-glucose (final concentration of D-glucose 75 μM). The medium is aspirated out. The pieces of tissue are washed several times and subsequently solubilized by alkali treatment for the determination of radioactivity. Table 1 shows the results.

TABLE 1

| | Glucose uptake | | | | | |
|---|---|---|---|---|---|---|
| | b) Diaphragm | | | a) Lipocytes | | |
| | Insulin [dpm] | Tri-peptide [dpm] | Hexa-peptide [dpm] | Insulin [dpm] | Tri-peptide [dpm] | Hexa-peptide [dpm] |
| 0.1 Mm | | 7591 | 7429 | | 1838 | 1488 |
| 0.5 Mm | | 8540 | 7752 | | 2947 | 1917 |
| 1 Mm | | 11588 | 8597 | | 6533 | 4218 |
| 0.5 ng | 10055 | | | 4379 | | |
| 5 ng | 20841 | | | 26312 | | |
| baseline | 7348 | | | 1235 | | |

Example 6

Glucose transport

Lipocytes and pieces of diaphragm are prepared as in Example 5. The following tests measure exclusively the specific glucose transport which can be stimulated by insulin (facilitated diffusion) through the plasma membrane by means of glucose carriers, including the insulin signal-transmission cascade. Any effect of glucose metabolism on glucose transport is ruled out by using the non-metabolizable glucose analog.

a) Rat lipocytes are incubated in the presence or absence of insulin or peptide with 2-deoxy-D-[1-$^3$H]-glucose (final concentration of D-glucose 0.2 mM) and L-[1-$^{14}$C]-glucose (not transportable). To determine the radioactivity ([$^3$H] and [$^{14}$C]) the cells are separated from the medium by centrifugation through an oil layer. The specific stereoselective glucose transport is calculated as the difference between the total cell-bound radioactivity ([$^3$H]-glucose) and the associated radioactivity due to diffusion and non-specific effects ([C]-glucose).

b) Pieces of diaphragm are incubated in the presence or absence of insulin or peptide with 2-deoxy-D-[1-$^3$H]-glucose (final concentration of D-glucose 0.1 mM) and L-[1-$^{14}$C]-glucose. The pieces of tissue are separated from the medium by rapid filtration through glass fiber filters and are thoroughly washed. The radioactivity is measured in an alkaline extract. Table 2 shows the results.

TABLE 2

| | Glucose transport | | | | | |
|---|---|---|---|---|---|---|
| | a) Lipocytes | | | b) Diaphragm | | |
| | Insulin [dpm] | Tri-peptide [dpm] | Hexa-peptide [dpm] | Insulin [dpm] | Tri-peptide [dpm] | Hexa-peptide [dpm] |
| 0.1 Mm | | 2289 | 2218 | | 8836 | 8450 |
| 0.5 Mm | | 3055 | 2842 | | 9822 | 8928 |
| 1 Mm | | 5781 | 3922 | | 11252 | 9676 |
| 0.5 ng | 4851 | | | 10828 | | |
| 5 ng | 20342 | | | 17750 | | |
| baseline | 2311 | | | 8522 | | |

Example 7

Esterification in vitro

This test measures the esterification of glycerol 3-phosphate which can be stimulated by insulin in lipid products (triglycerides, phospholipids). The enzymes of lipid synthesis (for example acyl-CoA: L-glycerol 3-phosphate acyltransferase) are involved in this, including a functional insulin signal-transmission cascade. Glucose transport plays no part in this, as is proved by the lack of inhibition of esterification by cytochalasin B.

Rat lipocytes prepared as in Example 5 are incubated with D-glucose (final concentration 33 μM) in the presence or absence of insulin or peptide, and subsequently treated with low concentrations of saponin to permeabilize the plasma membrane (without damaging internal membranes). The incubation is continued after addition of L-[U-$^{14}$C]-glycerol 3-phosphate. Toluene-soluble scintillation cocktail is added and the lipid is separated from the aqueous phase by centrifugation. The toluene phase containing the lipid is removed and its radioactivity is determined. Table 3 shows the results.

TABLE 3

| Esterification with lipocytes | | |
|---|---|---|
| | Insulin [dpm] | Tripeptide [dpm] |
| 0.1 Mm | | 3710 |
| 0.5 mM | | 4422 |
| 1 Mm | | 5398 |
| 0.5 ng | — | |
| 5 ng | 3640 | |
| baseline | 3842 | |

Example 8

Lipogenesis

Rat lipocytes from Example 5 are treated with low concentrations of trypsin to inactivate the insulin receptor by proteolysis. After addition of protease inhibitors, the cells are washed twice by flotation, and the incubation is continued at 37° C. for 15 min. These cells are then used for the test of stimulation of lipogenesis by the peptides. A control incubation with insulin shows that the trypsin-treated cells display only very little lipogenesis which can be stimulated by insulin and thus only a rather limited number of functional insulin receptors (with regard to insulin binding). This means that this test measures stimulation of lipogenesis owing to interventions in the insulin signal-transmission cascade after receptor binding of insulin. Table 4 shows the results.

TABLE 4

| Lipogenesis | | |
|---|---|---|
| | Insulin [dpm] | Tripeptide [dpm] |
| 0.1 Mm | | 3250 |
| 0.5 mM | | 4145 |

TABLE 4-continued

| Lipogenesis | | |
|---|---|---|
| | Insulin [dpm] | Tripeptide [dpm] |
| 1 Mm | | 5072 |
| 0.5 ng | — | |
| 5 ng | 3087 | |
| baseline | 2355 | |

Example 9

Blood glucose profile in mice

Female Charles River Wiga Balb-C mice weighing 17 to 21 g (about 30 days old) receive a standard diet. The mice receive no food for 16 hours before the start of the experiment. 5 animals in each experimental group receive intravenous administration of an aqueous solution (pH 6) of the compound from Example 4 (octapeptide). Volume administered 0.3 ml/animal.

Table 5 shows blood glucose levels as a percentage difference between the control group (5 animals, buffer solution pH 6.0; volume administered 0.3 ml/animal) and the animals with the octapeptide according to the invention. The average for each experimental group is indicated in each case.

TABLE 5

| | Blood glucose profile | |
|---|---|---|
| Time | Octapeptide [%] | |
| [minutes] | 500 μg/animal | 1000 μg/animal |
| 20 | −2 | −31 |
| 40 | −5 | −19 |
| 60 | −13 | −23 |
| 75 | −21 | −24 |
| 90 | −21 | −19 |

---

We claim:

1. A method comprising administering to a patient in need thereof an effective amount of a pharmaceutical composition for the treatment of diabetes mellitus or non-insulin-dependent diabetes comprising at least one peptide selected from the group consisting of Tyr-Gln-Leu-Glu-Asn-Tyr-Cys-Asn, Acetyl-Leu-Glu-Asn-Tyr-Cys-Asn-OH, Asn-Tyr-Cys-Asn, or $$X\text{-}Q\text{-}Cys\text{-}D \qquad (II)$$

where
Q is Tyr, His or Nal,
D is Asp, Asn, D-Asp, D-Ash, β-Ala or Azagly-NH$_2$,
X is
a) hydrogen or b) $(C_1\text{–}C_{18})\text{-alkyl-}\overset{\overset{\displaystyle O}{\|}}{C}-$, or the stereoisomeric forms of the peptide of the formula II, or physiologically tolerated salts of the peptide of the formula II.

2. The method as claimed in claim 1, comprising at least one peptide selected from the group consisting of His-Cys-Asn and Tyr-Cys-Asn.

3. A pharmaceutical composition which has an effective amount of at least one peptide selected from the group consisting of Tyr-Gln-Leu-Glu-Asn-Tyr-Cys-Asn, Acetyl-Leu-Glu-Asn-Tyr-Cys-Asn-OH, Asn-Tyr-Cys-Asn or a peptide of formula II as claimed in claim 1.

\* \* \* \* \*

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

Tyr  Gln  Leu  Glu  Asn  Tyr  Cys  Asn
    1                      5

( 2 ) INFORMATION FOR SEQ ID NO:2:

( i ) SEQUENCE CHARACTERISTICS:
        ( A ) LENGTH: 6 amino acids

```
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

Leu  Glu  Asn  Tyr  Cys  Asn
    1                  5

( 2 ) INFORMATION FOR SEQ ID NO:3:

( i ) SEQUENCE CHARACTERISTICS:
                ( A ) LENGTH: 4 amino acids
                ( B ) TYPE: amino acid
                ( C ) STRANDEDNESS: single
                ( D ) TOPOLOGY: linear ( i i ) MOLECULE TYPE: peptide ( x i ) SEQUENCE DESCRIPTION: SEQ ID NO:3:

Asn  Tyr  Cys  Asn
    1

( 2 ) INFORMATION FOR SEQ ID NO:4:

( i ) SEQUENCE CHARACTERISTICS:
                ( A ) LENGTH: 3 amino acids
                ( B ) TYPE: amino acid
                ( C ) STRANDEDNESS: single
                ( D ) TOPOLOGY: linear ( i i ) MOLECULE TYPE: peptide ( x i ) SEQUENCE DESCRIPTION: SEQ ID NO:4:

Tyr  Cys  Asn
    1
```